US010080685B2

(12) United States Patent
Weston et al.

(10) Patent No.: US 10,080,685 B2
(45) Date of Patent: Sep. 25, 2018

(54) TREPHINE GUIDE

(71) Applicant: Coronet Medical Technologies Ltd., Ripon (GB)

(72) Inventors: Philip Douglas Weston, Ripon (GB); Ian Douglas Weston, Ripon (GB)

(73) Assignee: Coronet Medical Technologies Ltd., Ripon (GB)

( * ) Notice: Subject to any disclaimer, the term of this patent is extended or adjusted under 35 U.S.C. 154(b) by 269 days.

(21) Appl. No.: 14/850,368

(22) Filed: Sep. 10, 2015

(65) Prior Publication Data
US 2016/0067096 A1 Mar. 10, 2016

(30) Foreign Application Priority Data
Sep. 10, 2014 (GB) .................................. 1416033.7

(51) Int. Cl.
*A61F 9/013* (2006.01)
(52) U.S. Cl.
CPC .................... *A61F 9/013* (2013.01)
(58) Field of Classification Search
CPC .......... A61F 9/013; A61F 9/025; A61F 9/026; A61F 2009/00872; A61B 17/3205
USPC ....................................................... 606/166
See application file for complete search history.

(56) References Cited

U.S. PATENT DOCUMENTS

| 4,319,575 A | 3/1982 | Bonte |
| 2002/0013579 A1* | 1/2002 | Silvestrini ............... A61F 9/013 606/32 |
| 2003/0045799 A1* | 3/2003 | Bazin ..................... A61B 5/448 600/476 |
| 2003/0050561 A1* | 3/2003 | Bazin ..................... A61B 5/448 600/476 |
| 2007/0173791 A1 | 7/2007 | Raksi |

(Continued)

FOREIGN PATENT DOCUMENTS

| EP | 1273278 A2 | 1/2003 |
| EP | 2191799 A1 | 6/2010 |
| WO | 9517144 | 6/1995 |

(Continued)

OTHER PUBLICATIONS

Response to European Search Opinion from counterpart European Application No. 15184428.9, dated Jul. 7, 2016, 6 pp.

(Continued)

*Primary Examiner* — Christopher L Templeton
*Assistant Examiner* — George J Ulsh
(74) *Attorney, Agent, or Firm* — Shumaker & Sieffert, P.A.

(57) ABSTRACT

There is disclosed a trephine guide having an upper guide member having a first substantially circular guide aperture and a first circumferential portion and a lower guide member having a second substantially circular guide aperture and a second circumferential portion. The upper and lower guide members are connected in a spaced apart configuration by at least one arm extending from the first circumferential portion to the second circumferential portion, such that the first and second guide apertures are substantially concentric, thereby to allow a trephine to pass through the upper and lower guide members. The at least one arm has a width that extends over less than three quarters of the circumference of the first or second circumferential portions to allow good visibility to a trephine blade.

18 Claims, 6 Drawing Sheets

(56) References Cited

U.S. PATENT DOCUMENTS

2010/0152754 A1* 6/2010 Weston ................ A61F 9/013
606/166
2013/0035674 A1* 2/2013 Lummis ................ A61F 9/009
606/5

FOREIGN PATENT DOCUMENTS

| WO | 9903433 | 1/1999 |
|----|---------|--------|
| WO | 9917673 | 4/1999 |
| WO | 2005030102 A1 | 4/2005 |

OTHER PUBLICATIONS

European Communication from counterpart European Application No. 15184428.9, dated Feb. 20, 2017, 5 pp.
Examination and Search Report for corresponding application No. GB1416033.7, dated Mar. 9, 2015 (7 pgs.).
European Extended Search Report from counterpart European Application No. 15184428.9, dated Jan. 19, 2016, 7 pp.
Search and Examination Report from counterpart GB Patent Application GB 1416033.7, dated Dec. 19, 2017, 5 pp.

* cited by examiner

TREPHINE GUIDE

CROSS REFERENCE TO RELATED APPLICATION

This application claims priority to GB Application No. 1416033.7, filed Sep. 10, 2014, which is incorporated by reference herein in its entirety.

There is disclosed a trephine guide for use in ophthalmic surgery, particularly but not exclusively in the field of corneal graft surgery and/or penetrating keratoplasty.

BACKGROUND

A trephine is a surgical instrument having a cylindrical blade. Particular types of trephine are used in ophthalmic surgery to cut buttons from donor corneal grafts, and also to cut away diseased sections of a patient's cornea.

Typical corneal trephines are known, for example, from U.S. Pat. No. 4,319,575 and U.S. Pat. No. 2,473,968, the disclosures of which are hereby incorporated into the present application by reference.

A more recent development in trephine technology comprises an outer, generally cylindrical casing with an annular base and an inner, cylindrical tube of slightly smaller diameter than the outer casing and also having an annular base, slightly recessed from the annular base of the outer casing. This allows the base of the casing to be placed on the curved cornea, with the recessed base of the tube also resting on the epithelium as a result of the convex curvature of the cornea. When a vacuum is applied to the cylindrical space between the outer casing and the inner tube, the casing becomes attached to the epithelium by suction, thereby preventing movement between the casing and the cornea. A cylindrical trephine blade is mounted inside the inner tube and provided with a screw mechanism so as to allow the blade to be raised and lowered within the inner tube. A spoked wheel is provided at an end of the trephine remote from the base so as to allow the amount the blade is raised and lowered to be determined by a number of turns or fractions of turns of the spoked wheel.

In use, the trephine is examined under an operating microscope and the spoked wheel is turned until the blade of the trephine is aligned with the base of the inner tube, this being the zero position. The blade is then retracted by turning the spoked wheel anticlockwise so as to ensure that the blade does not touch the cornea when the vacuum trephine assembly is placed on the epithelium with both the base of the casing and the base of the inner tube contacting the epithelial surface of the cornea. If the blade is not sufficiently retracted, the blade is forced into the cornea.

A vacuum is then applied to the cylindrical space between the casing and the inner tube, for example by using a syringe with a flexible tube connected to the annular space.

Once a good vacuum seal has been obtained and the assembly is fixed to the cornea by suction, the spoked wheel is rotated clockwise until the blade touches the cornea (this will generally be slightly behind the zero position due to the convex curvature of the cornea), and cutting then starts by continuing to rotate the spoked wheel a desired number of turns. In currently available embodiments of this type of vacuum trephine, each complete revolution of the spoked wheel raises or lowers the blade of the trephine by approximately 0.25 mm relative to the casing and the inner tube. At the desired depth of cut, the vacuum is released by operating the syringe appropriately, and the trephine is then lifted from the patient's eye.

While operation of the vacuum trephine has been described with reference to a living patient, it may also be used to cut a button from a donor corneal graft harvested from a cadaver and mounted on an artificial anterior chamber.

EP2191799 discloses a trephine apparatus with a transparent casing having an outer casing and an inner casing. A vacuum or partial vacuum may be applied to the space between the outer casing and the inner casing using a suction pump. This enables the trephine apparatus to be releasably attached to the surface of the eyeball. The outer and inner casings are formed from a non-opaque material to improve the user's visibility of the blade.

Some transparent casings may still obscure the user's visibility of the trephine blade.

Furthermore, there are difficulties with existing vacuum trephine devices relating to the fit of the vacuum trephine device on the eye. No two eyes are identical and therefore accommodating for the individual form of the eye can be challenging and costly. Again, this may be compensated for by increasing the strength of the vacuum in the vacuum chamber, but this can cause damage or scarring to the eye.

BRIEF SUMMARY OF THE DISCLOSURE

According to a first aspect there is provided a trephine guide comprising:
- an upper guide member having a first substantially circular guide aperture and a first circumferential portion;
- a lower guide member having a second substantially circular guide aperture and a second circumferential portion;
- wherein the upper and lower guide members are connected in a spaced apart configuration by at least one arm extending from the first circumferential portion to the second circumferential portion, such that the first and second guide apertures are substantially concentric, thereby to allow a trephine to pass through the upper and lower guide members;
- wherein the circumferential portion of the lower guide member, on its bottom surface, is provided with an annular channel that is open at the bottom surface, the channel being provided with means for connection to a vacuum source;
- wherein the annular channel is defined by an outer circumferential wall and an inner circumferential wall; and
- wherein the outer circumferential wall comprises or is provided with a flexible skirt for contacting a corneal surface of an eye.

One benefit is that the trephine guide has an open structure that provides less obstruction of the view to a trephine being guided through the guide. The at least one arm therefore defines a window for providing an unobstructed view of the trephine as it approaches a surface of an eye. As such, a user can easily see the trephine and perform more accurate operations than previously possible.

Optionally, the width of the arm is less than one half or less than one third of the circumference of the first or second circumferential portions.

In some embodiments, first and second arms may be provided. The second arm may be arranged generally opposite the first arm, and the first and second arms may be shaped so as to define windows for viewing the trephine.

Optionally multiple windows are provided, defined by multiple arms.

Optionally, the at least one arm defines a window, and optionally, the window is filled with a substantially non-opaque material. Alternatively, the window may simply comprise an empty space.

The outer circumferential wall may project further from the bottom surface of the lower guide member than the inner circumferential wall so as to help ensure that both circumferential walls contact the curved corneal surface of an eye when placed appropriately thereupon.

A vacuum or partial vacuum may then be applied to the channel between the outer and inner circumferential walls, for example by way of a vacuum pump and luer or other connection that communicates with the channel, thereby to cause the trephine guide to become releasably attached to the surface of the eye when in position.

The outer circumferential wall may comprise or may be provided with a flexible skirt for contacting the corneal surface of the eye. The skirt may be made of a soft, resilient biocompatible material.

The flexible skirt provides improved tolerance and enables improved contact with the corneal surface. The benefit is that a good vacuum connection to a wider range of eyeball sizes may be obtained by the trephine guide because of the flexible skirt. Furthermore, the level of suction required to form a vacuum within the space in the channel is less than that required by existing vacuum trephines.

The flexible skirt is preferably flared radially outwardly from the lower guide member. Flaring the flexible skirt allows for improved fit for a greater variety of different eyes and provides additional size variability, enabling the trephine guide to form a good fit with a broader size distribution of surface profiles of the eye.

The vacuum pressure of the device on the surface of the eye is due to the increased vacuum area on the eye's surface.

Optionally, the flexible skirt is tapered in thickness.

Optionally, the flexible skirt is formed from a transparent or non-opaque material.

Optionally, the upper and/or the lower member is provided with thumb and finger grips.

The upper and/or lower guide members, and optionally also the at least one arm, portion may be made of a non-opaque material.

The non-opaque material may be substantially transparent, and may be made of a surgical grade plastics material such as a polycarbonate or the like.

Optionally, the upper and/or lower guide member is/are provided with means for facilitating gripping thereof by a surgeon during use. For example, the outside surface may be roughened or ridged, or may include at least one pair of opposed projecting members having, respectively, finger and thumb rests.

In addition to providing good edge-on lateral visibility of the base of the lower guide member and the trephine, the use of non-opaque, preferably substantially transparent plastics materials (as opposed to opaque metal materials, for example) in the trephine guide allow the assembly to be made less heavy and potentially assists in positional stability by lowering the centre of mass of the trephine guide (since plastics materials generally have lower density than metallic materials). Moreover, modern plastics moulding techniques can allow a greater degree of manufacturing accuracy to be achieved than traditional metal milling techniques.

In some embodiments, the entire trephine guide is made of a substantially non-opaque material such as a transparent plastics material. In other embodiments, just the lower guide member is made of a non-opaque material.

This provides the advantage that the base of the lower guide member and the trephine blade can be viewed edge-on through the non-opaque material with a microscope without parallax. This allows the zero position of the blade to be set easily and highly accurately in a manner not possible with existing vacuum trephine assemblies.

According to a further aspect there is provided a trephine comprising a trephine blade positioned at one end of a substantially cylindrical holder, the holder being sized and configured to fit rotatably inside the trephine guide.

The holder may be provided with drive means adapted to engage corresponding drive means provided in the first and/or second circular guide apertures of the trephine guide so as to allow raising and lowering of the blade with respect to the lower guide member by rotating the holder clockwise or anticlockwise. The drive means may comprise complementary screw threads. Rotating the holder results in the holder being raised or lowered relative to the lower guide member.

An end of the holder remote from the blade may be provided with a spoked wheel, capstan or other means for facilitating rotation of the holder and providing easy reference to a surgeon as to how many turns or fractions of turns the holder is rotated during operation.

Optionally, the cylindrical trephine blade is configured to be raised and lowered in in a continual manner and has a range of approximately 0 to 15 mm, or approximately 0.5 to 15 mm, or approximately 0.5 to 10 mm, depending upon the spacing between the upper guide member and the lower guide member.

One full rotation of the capstan may correspond to a trephine blade travel relative to the lower guide member, between approximately 100 μm to approximately 500 μm. Optionally, one full rotation of the spoked wheel raises or lowers the trephine blade by 250 μm.

The holder and/or the means for facilitating rotation may be made of a surgical grade metal or plastics material. The blade is typically made of surgical grade metal or ceramic.

The trephine blade and/or the trephine holder may be provided with an aligner. The aligner may be cross wires. A circle may also be provided at/or close to the cross of the cross wires or alternatively, the circle may replace the cross of the cross wires to facilitate alignment of the trephine guide on the eye.

Optionally, the trephine may include a tube positioned inside the cylindrical holder (in embodiments where the cylindrical holder is hollow) and/or the trephine blade.

The tube is adapted to control the incision depth. The tube may include an aligner. The tube may be adjustably moveable within the trephine so as to allow different incision depths to be set. This may be achieved by way of the tube having a screw thread on its outer circumferential surface that engages with a complementary screw thread provided in an inner circumferential surface of the trephine holder.

The tube may be an open ended tube having a lower rim for contacting the surface of the eye. The lower rim may be tapered or flared to complement the curvature of the surface of the eye. In this arrangement, only the lower rim of the tube contacts the surface of the eye.

Alternatively, the tube may be a closed tube, and in use, a closed end of closed tube contacts the surface of the eye.

In these embodiments, the lower rim or closed end of the tube will abut the corneal surface of the eye when a preset cutting depth is reached, thereby preventing or resisting further downward cutting movement of the trephine relative to the corneal surface.

According to a further aspect there is provided a system comprising a trephine guide and a trephine of the foregoing aspects.

BRIEF DESCRIPTION OF THE DRAWINGS

For a better understanding of the present invention and to show how it may be carried into effect, reference shall now be made by way of example to the accompanying drawings, in which.

DETAILED DESCRIPTION

Figure 1:
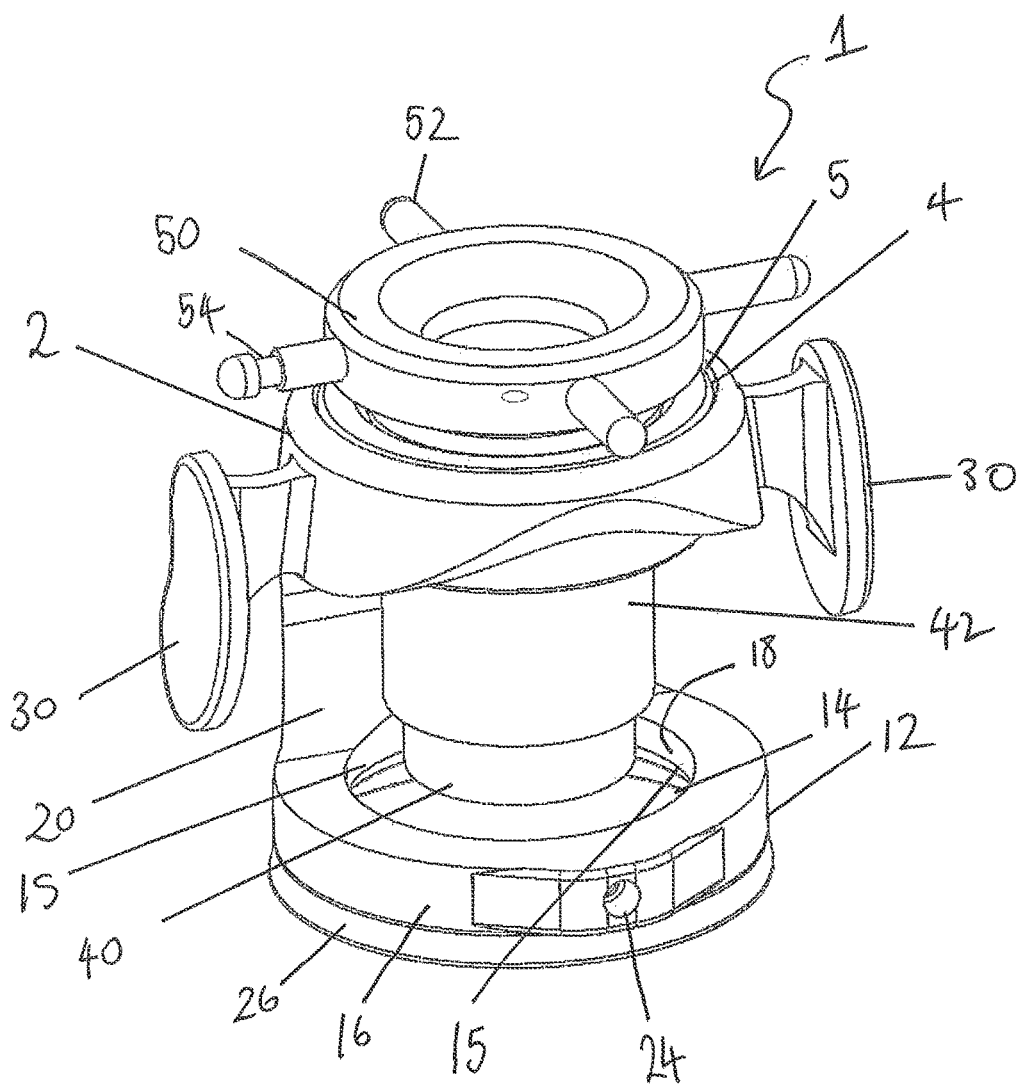
FIG. 1 shows a three-dimensional view of an example of a trephine guide.

Throughout the drawings, like features have been labelled using like reference numerals, albeit in some cases incremented by 100.

With reference to FIG. 1, there is shown a trephine guide 1 comprising an upper guide member 2 having formed therein a first substantially circular guide aperture 4 and a lower guide member 12 having formed therein a second substantially circular guide aperture 14. The upper and lower guide members 2, 12 are connected to each other in a spaced apart configuration by an arm 20. The upper 2 and lower 12 guide members each have respective circumferential portions 5, 15 defining the guide apertures 4, 14, and are arranged in a spaced apart arrangement such that the guide apertures 4, 14 are substantially concentric. The guide apertures 4, 14 are shaped to guide a trephine blade 40 held in a trephine holder 42, through the trephine guide 1.

The arm 20 is configured to position the upper and lower guide members 2, 12 within closely defined tolerances while allowing a clear substantially unobstructed view of the trephine blade 40 as it approached the surface of an eyeball. This also allows a surgeon easily to observe the progress of, for example, a keratoplasty procedure without having to adjust for parallax because the surgeon has a clear view of the blade 40 and the curved surface of the eye. The width of the arm 20 in the illustrated embodiment is less than one third of the circumference of the circumferential portions 5, 15.

The upper guide member 2 includes a pair of opposed projecting members 30 having, respectively, finger and thumb rests. The projecting members project from the upper guide member 2. Alternatively or in addition, finger and thumb rests may be provided on the lower guide member 12 in similar fashion.

A circumferential portion 15 of the lower guide member 12, on its bottom surface, is provided with an annular channel that is open at the bottom surface. The annular channel is provided a connector or luer 24 for connection to a vacuum.

The annular channel 22 is defined by an outer circumferential wall 16 and an inner circumferential wall 18. The outer circumferential wall 16 may project further from the bottom surface of the lower guide member 12 than the inner circumferential wall 18 so as to help ensure that both circumferential walls 16, 18 contact the curved surface of an eye when placed appropriately thereupon.

The channel 22 is connected to a vacuum pump (not shown) via a connector or luer 24. A vacuum or partial vacuum is applied to a volume between the outer and inner walls 16, 18 by way of the vacuum pump connected to the luer 24 or the like that communicates with the channel 22, thereby to cause the trephine guide 1 to become releasably attached to the curved corneal surface of the eye 28 when in position.

The outer circumferential wall 16 extends beyond the inner circumferential wall 18 so as to form a better fit with the convex surface 28 of the eyeball.

A substantially cylindrical trephine blade 40 and blade holder 42 can be passed through the upper and lower guide apertures 4, 14 such that the blade 40 can be raised and lowered relative to the lower guide member 12.

A base portion of the outer circumferential wall 16 of the lower guide member 12 is provided with a flexible skirt 26. The flexible skirt 26 is formed from biocompatible material such as silicone; however any elastomeric material able to carry out the same function is envisaged. In one example, the flexible skirt is formed from transparent material.

The flexible skirt 26 is flared radially outwardly from the lower guide portion 12. The skirt 26 extends beyond the inner circumferential wall 18 to accommodate the convex shape of the surface 28 of an eyeball.

In use, as the trephine guide 1 is moved towards the surface 28 of the eyeball, the flexible skirt 26 is the first point of contact with the surface 28. The skirt 26 is able to flex or glide on the surface 28 of the eyeball creating a good fit, and can accommodate small undulations of the corneal surface 28 without difficulty. The skirt 28 tapers to a thin edge 27, which helps to form a good vacuum seal. A vacuum or partial vacuum is formed in the channel 22 between the outer wall 18 and the inner wall 16. A suction pump is connected via a tube or pipe to an inlet 24 to create a vacuum or partial in the channel 22. The level of suction required releasably to attach the trephine guide 1 to the surface 28 of the eyeball is lower than in a conventional vacuum trephine apparatus without a flexible skirt 26 because the flexible skirt 26 flexes toward the surface 28 of the eyeball to form a good attachment of the trephine guide 1 to the surface of the eyeball 28.

The trephine guide 1 is adapted to receive and guide a trephine towards the surface of the eye. The trephine includes a trephine blade 40 positioned at one end of a substantially cylindrical holder 42, the holder 42 being sized and configured to fit rotatably inside the trephine guide 1, inside the guide apertures 4, 14 of the upper and lower guide members 2, 12 of the trephine guide 1.

The holder 42 is provided with a screw thread adapted to engage with a complementary thread provided on an inner surface of at least one of the guide apertures 4, 14 so as to allow raising and lowering of the blade 40 by rotating the holder 42 clockwise or anticlockwise. Rotation of the holder 42 thereby translates into a raising or lowering movement of the trephine blade 40 relative to the lower guide member 12. In certain embodiments, complementary screw threads on the cylindrical holder 42 and one or other or both of the upper and lower guide members 2, 12 are employed.

An end of the holder 42 remote from the blade 40 may be provided with a capstan, or a spoked or knurled wheel 50 or other means for facilitating rotation of the holder 42 and providing easy reference to a surgeon as to how many turns or fractions of turns the holder 42 is rotated during operation. The capstan 50 is provided with outwardly protruding spokes 52. At least one of the spokes is provided with a reference marker 54 to indicate the relative position of the trephine blade 40 with respect to the upper and lower guide members 2, 12. One rotation of the capstan 50 causes the trephine blade to more 250 microns towards or away from the lower guide member 12.

The holder 42 and/or the means for facilitating rotation may be made of a surgical grade metal or plastics material.

The arrangement of the trephine guide 1 provides improved visibility to the trephine blade 40 while in use. The apparatus maintains structural integrity as the upper guide member 2 and the lower guide member 12 are spaced apart by the arm 20 which is shaped to ensure mechanical integrity of the trephine guide 1. In some examples, the arm 20 is reinforced.

Figure 2:
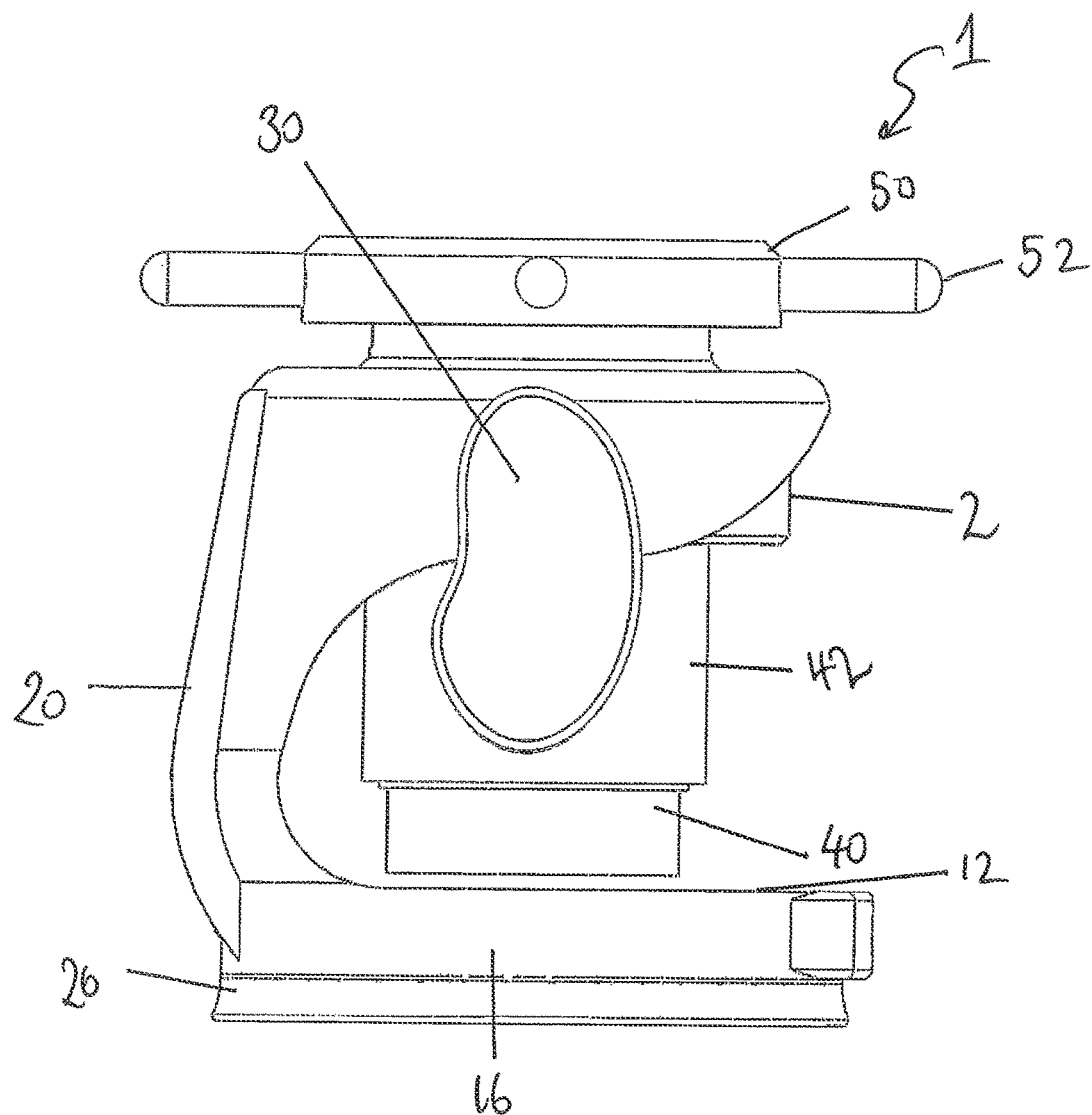
FIG. 2 shows a side view of the trephine guide.

FIG. 2 shows a side view of the trephine guide. The arm 20 is slightly convex to follow the general cylindrical form of the upper and lower guide members 2, 12 and to provide structural integrity to the upper and lower guide members 2, 12 to ensure the upper and lower guide members are resiliently spaced apart. The arm 20, and the upper and lower guide members 2, 12 define a window for observing the trephine blade 40 as it travels towards the surface of the eye.

Figure 3:
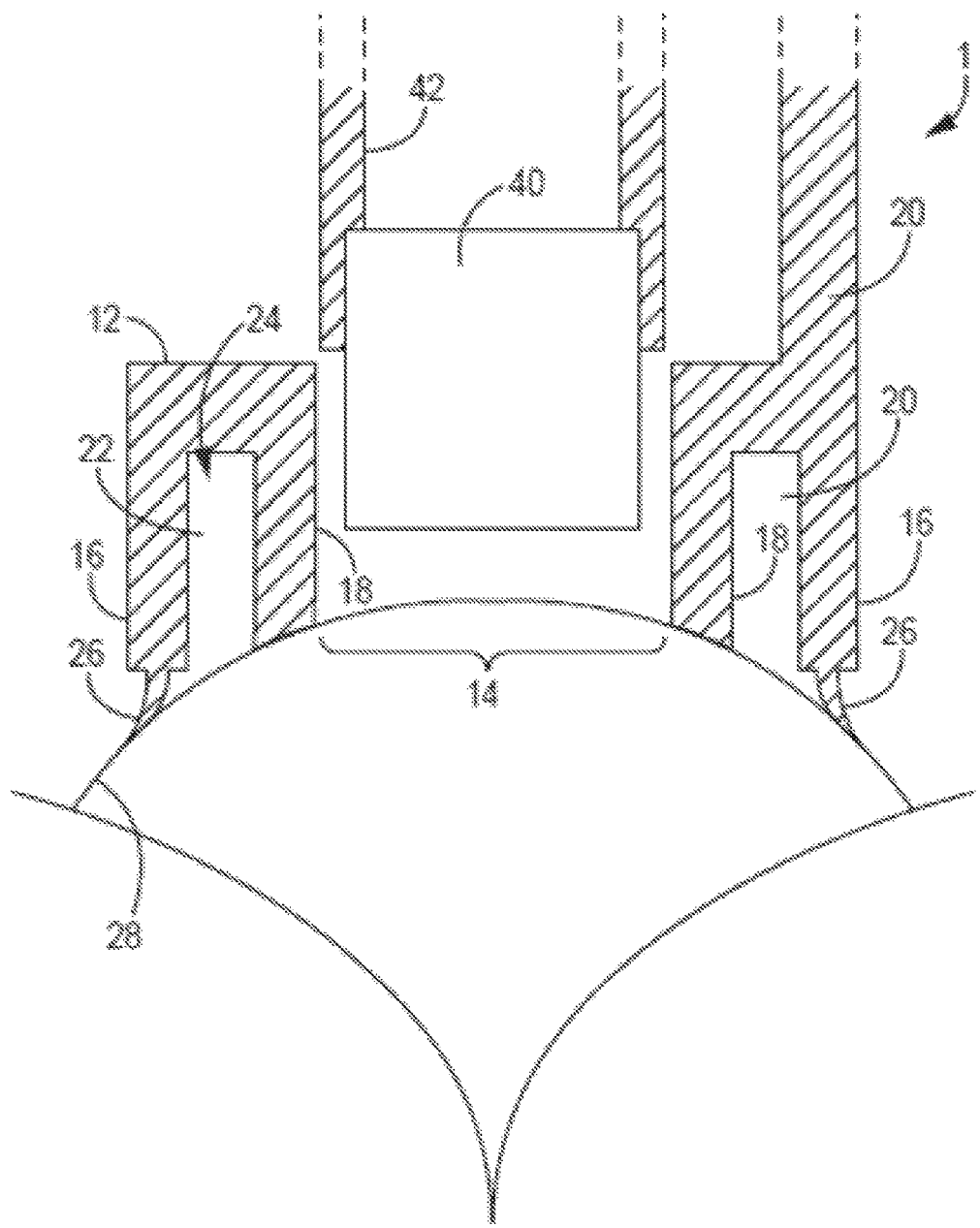
FIG. 3 shows a sketch of an example of a trephine guide in cross-section, the example shown resting on an eyeball.

FIG. 3 shows a sketch of the trephine guide 1 guiding a trephine blade 40 towards the surface of the eye 28. The outer circumferential wall 16 extends beyond the inner circumferential wall 18 of the lower guide member so that both walls contact the curved surface of the eye 28 simultaneously. Obviously, the exact height of the walls will depend on the curvature of a particular eye. The flexible skirt 26 provides a buffer to accommodate different curvatures of the surface of the eye 28 while also being able to accommodate small undulations in the surface of the eye.

Figure 4:
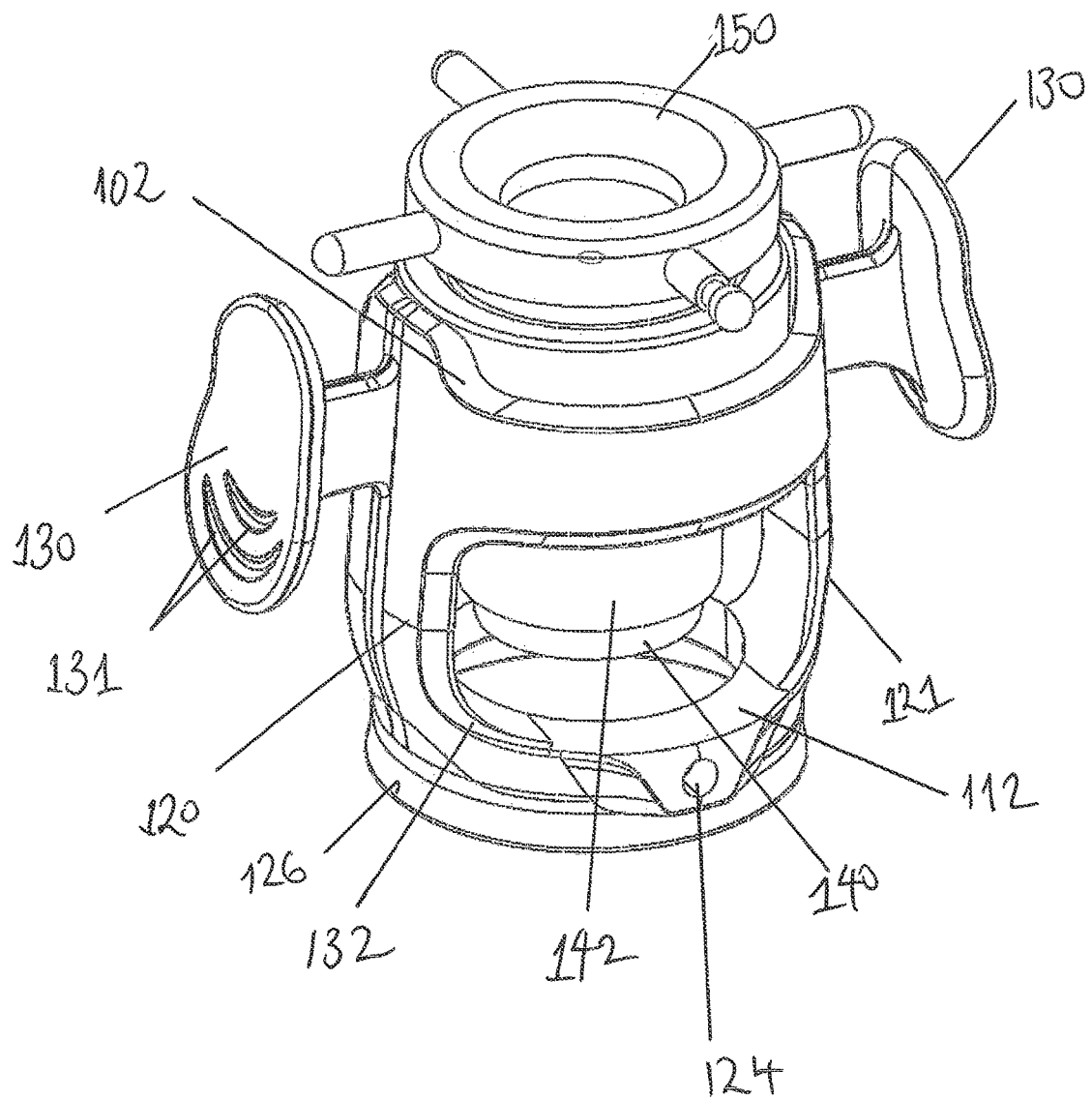
FIG. 4 a three-dimensional view of an example of a trephine guide.

FIG. 4 shows a trephine guide 100 provided with first and second arms 120, 121. The second arm 121 is arranged generally opposite to the first arm 120 and the arms 120, 121 are shaped to define a number of large windows 132 for viewing the trephine. The arms 120, 121 have tapered edges. The tapering is formed so that the edge of the arm 120, 121 is thinner than the cross-section of the arm 120, 121 to improve visibility to the trephine blade 140.

The windows 132 are provided on either side of the trephine guide 100. The lower guide member 112 includes a channel for forming a vacuum or partial vacuum as previously described. An inlet 124 is provided for a suction pump.

The upper guide member 102 includes one pair of opposed projecting members 130 having, respectively, finger and thumb rests. The projecting members project from the upper guide member 102. Alternatively or in addition, projecting members with finger and thumb rests may project from the arms 120, 121 or from the lower guide member 103.

The opposed projecting members are provided with protruding grips or indentations 131.

The finger and thumb rests 130 project from the upper guide member 102 to provide convenient holding positions for the user. The finger and thumb rests 130 are located on the opposite sides of the trephine guide 100 and project from regions of the upper guide member 102 where the arms 120, 121 connect to the circumferential portion thereof. This helps to prevent a surgeon's finger and thumb from covering the windows 120 and blocking the view to the trephine blade 140.

Figure 5:
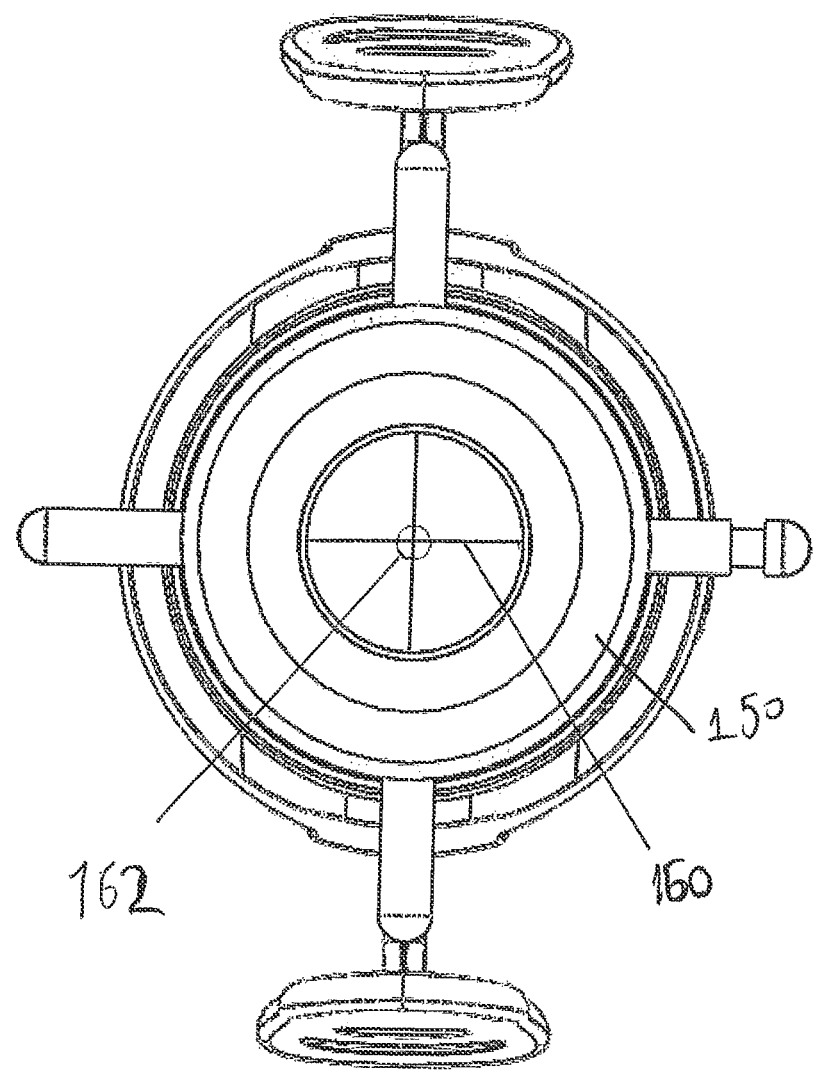
FIG. 5 shows an example of a trephine guide of the top looking down.

FIG. 5 shows the trephine guide looking down from the top showing the trephine. The trephine includes a trephine blade positioned at one end of a substantially cylindrical holder is positioned inside the trephine guide. The holder is sized and configured to fit rotatably inside the trephine guide.

A trephine is provided with an alignment feature 160 to aid the surgeon in positioning the trephine guide on a patient's eye, and to aid the positioning of the trephine blade as it is lowered towards the surface of the eye. A circle is also provided to aid in centring the trephine guide on the surface of the eye.

Figure 6:
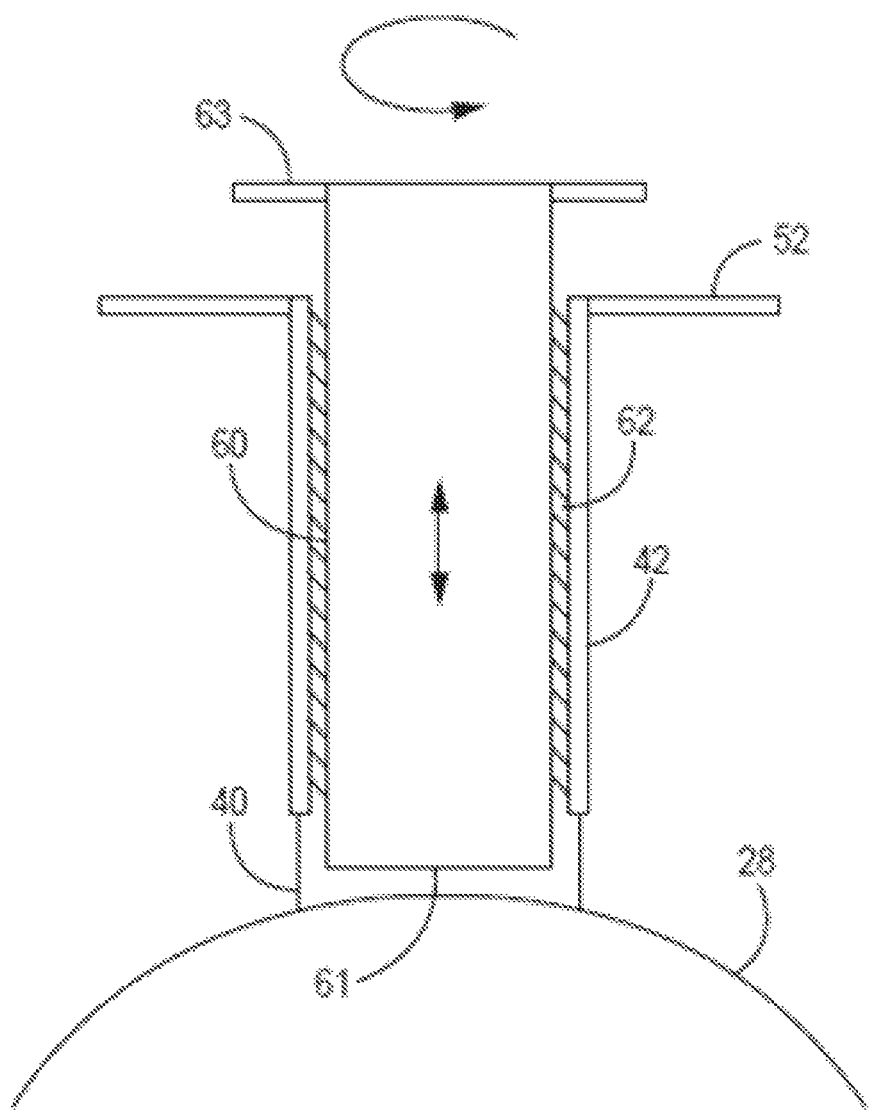
FIG. 6 shows an example of a trephine for use with the trephine guide of FIGS. 1 to 5.

FIG. 6 shows an embodiment comprising a trephine blade 40 mounted on the end of a substantially cylindrical holder 42. An upper end of the holder 42 is provided with a capstan having outwardly protruding spokes 52. The trephine blade 40 is shown resting on the surface 28 of an eyeball. The trephine shown in FIG. 5 is suitable for use with the trephine guide described hereinbefore. The trephine further includes a tube 60 positioned inside the holder 42 and/or the trephine blade 40. The tube 60 is configured to operate as a depth limiter for the trephine blade 40, preventing the trephine blade 40 from cutting beyond a depth set by a position of the lower end of the tube 60.

The tube 60 is fitted inside the holder 42, and a lower end 61 of the tube 60 resides in the space bound by inner walls of the holder 42 and the trephine blade 40. The tube 60 is mounted in such a way that when the tube 60 is rotated, the tube 60 cooperates with the inner walls of the holder 42 and the trephine blade 40 so that it advances and retracts by a determinable distance in relation to a cutting edge of the trephine blade 42. This may be by way of complementary screw threads 62 on the inner circumferential surface of the holder 42 and the outer circumferential surface of the tube 60. A capstan or spoked or knurled wheel 63 may be provided at the upper end of the tube 60 so as to allow ease of adjustment by a surgeon, thereby to set a predetermined cutting depth.

The capstan 63 may be provided with or interact with a dial or other indicia, which may be printed, etched, or may be moulded in profile. The dial (not shown) displays a range of digits and/or markers. The tube 60 may be further provided with an indicator to allow the user to determine the position of the end 61 of the tube 60 in relation to the cutting edge of the trephine blade 40.

For example, if the dial includes a scale from 0 to 9, when the indicator of the tube 60 intersects the marker 0, then the base 61 of the tube 60 is in alignment with the bottom of the cutting blade 40, and therefore the depth of cut is zero as the base 61 of the tube 60 prevents the blade 40 from forming a cut. When the tube 60 is rotated, the tube 60 retracts relative to the trephine blade 40 in order to expose the cutting edge of the trephine blade 40. For example, if the tube 60 is rotated so that the indicator of the tube 60 intersects the marker 3, then the depth of cut into a surface will be limited to 300 μm.

The depth of cut is limited by the position of the lower end 61 of the tube 60 relative to the trephine blade 40. In operation, the lower end 61 of the tube 60 is set at a desired relative position, and the trephine is inserted into the trephine guide 1. The trephine and its blade 40 can be raised or lowered relative to the trephine guide 1 by rotating the capstan 50, which the position of the base 61 of the tube 60 can be raised or lowered relative to the trephine blade 40 by rotating the capstan 63. When the trephine guide 1 is affixed to the surface 28 of the eyeball in the correct position by way of suction, the trephine blade 40 is lowered by turning the capstan 50, thereby to excise a corneal disc from the surface 28 of the eyeball. In addition to the depth of cut being determined by the degree of rotation of the capstan 50, the lower end 61 of the tube 60 acts as an additional safety limiter to prevent cutting beyond a predetermined depth, even in the event that the surgeon accidentally rotates the capstan 50 too far. In this manner, when an incision is made in a cornea for example, the blade 40 incises the cornea until the base 61 of the tube 60 comes into contact with the cornea. At this point the base 61 of the tube 60 physically prevents the cornea from travelling any further up the blade 40, or similarly, the base 61 of the tube 60 obstructs the blade 40 travelling any further into the cornea.

Improvements in manufacturing allow very precise control of the position of the tube 60 within the trephine blade 40, and as such, precise incision depths can be carried out. During manufacture of the trephine guide 1, the tube 60 may be positioned to a zero position, i.e. where the base 61 of the tube 60 is in line with the cutting edge of the blade 40 and thereby prevents an inadvertent incision. Calibration of the tube position relative to the cutting edge of the trephine blade 40 may be carried out by a computer controlled machine to ensure a high level of accuracy. Once the base 61 of the tube 60 and the cutting edge of the trephine blade 40 are in alignment, the indicator is added to the tube to indicate the 'zero' position. There are alternative ways of achieving the same task under the same conditions. For example, instead of the marker being added to the tube, the dial on the top of the trephine guide 1 could be rotated to match the indicator of the tube and thereby calibrate the tube relative to the trephine blade 40.

In an example the tube includes an aligner as described above to aid the alignment of the trephine blade 40 on the surface 28 of the eye.

The tube 60 may be an open ended tube, and the rim of the lower end 61 of the tube 60 may be tapered to complement the curvature of the surface 28 of the eye. In this arrangement, only the rim of the end 61 of the tube 60 contacts the surface 28 of the eye.

Alternatively, the tube 60 may be solid or have a closed lower end 61, and the entire lower end 61 may contacts the surface 28 of the eye at the predetermined cutting depth. In this embodiment, the closed lower end 61 may be substantially flat, or it may be slightly concave so as to accommodate the curvature of the surface 28 of the eyeball.

In certain embodiments, at least a base portion of the lower guide portion 12, 112 is made of a non-opaque, preferably substantially transparent material, although in some embodiments the entire trephine guide 1, 100 is substantially transparent.

In embodiments in which the lower guide member 12, 112 of the trephine guide 1, 100 is transparent or at least non-opaque, it is possible to observe the position of the trephine blade directly from the side without any optical effects such as parallax.

Furthermore, the large windows 132 in one example provide a clear view through the outer casing to the blade.

The flexible skirt 26 may be cylindrical and not have a flared profile extending from the lower guide portion 12.

With the above described arrangement, the trephine guide 1 provides improved tolerance of fit and enables improved contact with the surface 28 of an eyeball because the flexible skirt 26 provides a flexible attachment means to the surface 28 of the eyeball. One benefit is that a wider range of eyeball sizes and small undulations of the eyeball surface may be accommodated by the apparatus because of the flexible skirt 26.

Furthermore, the level of suction required to form a vacuum within the channel 22 is less than that required by existing vacuum trephines. Since less suction is required, the surface of the cornea is less deformed and the trephine blade is able to perform a more accurate incision into the cornea because the cornea is less deformed so the profile of a cut from the trephine is closer to being perpendicular to the plane formed by the trephine cutting edge.

The flexible skirt provides a larger more stable base than existing trephine guides. The channel can be configured to contact the surface of the eye in the limbus region rather than the corneal region. In this manner, the trephine guide is more stable because the limbus provides a more resilient platform for the trephine guide. The vacuum therefore acts on the limbus region and not on the more fragile corneal region. One added benefit of this arrangement is that the vacuum is not applied to the corneal region and the corneal region is not deformed during the cutting process.

The trephine guide provides an improved guide allowing excellent visualisation of a trephine blade as it travels through the trephine guide and approaches the curved cornea surface of the eye because the upper and lower guide are separated by an arm that defines a large window for direct visualisation of the trephine blade.

It will be clear to a person skilled in the art that features described in relation to any of the embodiments described above can be applicable interchangeably between the different embodiments. The embodiments described above are examples to illustrate various features of the invention Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A trephine guide comprising:
   an upper guide member having a first substantially circular guide aperture and a first circumferential portion;
   a lower guide member having a second substantially circular guide aperture and a second circumferential portion;

wherein the upper and lower guide members are connected in a spaced apart configuration by at least one arm extending from the first circumferential portion to the second circumferential portion, such that the first and second guide apertures are substantially concentric, thereby to allow a trephine to pass through the upper and lower guide members;

wherein the circumferential portion of the lower guide member, on its bottom surface, is provided with an annular channel that is open at the bottom surface, the channel being connectable to a vacuum source;

wherein the annular channel is defined by an outer circumferential wall and an inner circumferential wall; and wherein the outer circumferential wall comprises a soft, flexible skirt for contacting a corneal surface of an eye, and wherein the outer circumferential wall is configured to avoid deformation of the corneal surface when vacuum is applied by the vacuum source.

2. The trephine guide as claimed in claim 1, wherein the at least one arm has a width that extends over less than three quarters of the circumference of the first or second circumferential portions.

3. The trephine guide as claimed in claim 1, wherein the at least one arm has a width that extends over less than half of the circumference of the first or second circumferential portions.

4. The trephine guide as claimed in claim 1, wherein the at least one arm has a width that extends over less than one third of the circumference of the first or second circumferential portions.

5. The trephine guide as claimed in claim 1, wherein the at least one arm comprises at least first and second arms that define at least first and second windows through which an interior of the trephine guide can be viewed.

6. The trephine guide as claimed in claim 1, wherein the outer circumferential wall projects further from the bottom surface of the lower guide member than the inner circumferential wall.

7. The trephine guide as claimed in claim 1, wherein the flexible skirt is flared radially outwardly from the lower guide member.

8. The trephine guide as claimed in claim 1, wherein the flexible skirt has a tapered profile.

9. The trephine guide as claimed in claim 1, wherein the flexible skirt comprises a transparent material.

10. The trephine guide as claimed in claim 1, wherein the upper guide member comprises a substantially non-opaque material.

11. The trephine guide as claimed in claim 10, wherein the substantially non-opaque material is substantially transparent.

12. The trephine guide as claimed in claim 1, wherein the lower guide member comprises a substantially non-opaque material.

13. A trephine comprising a trephine blade positioned at one end of a substantially cylindrical holder, the holder fit rotatably inside the trephine guide of claim 1.

14. The trephine as claimed in claim 13, wherein the holder comprises a screw thread adapted to engage a corresponding screw thread provided in first and/or second circular guide apertures of the trephine guide so as to allow raising and lowering of the blade with respect to the lower guide member by rotating the holder clockwise or anticlockwise.

15. The trephine as claimed in claim 13, wherein an end of the holder remote from the blade is provided with a spoked or a knurled wheel or a capstan for facilitating rotation of the holder.

16. The trephine as claimed in claim 13, wherein the trephine further includes a tube positioned inside the cylindrical holder and/or the trephine blade to control a depth of incision into a surface of an eye.

17. The trephine as claimed in claim 16, wherein the tube is an open-ended tube having a lower rim for contacting the surface of the eye.

18. The trephine as claimed in claim 17, wherein the lower rim has a tapered profile to complement a curvature of the surface of the eye.

* * * * *